United States Patent
Montano, Jr. et al.

[11] Patent Number: 5,813,405
[45] Date of Patent: Sep. 29, 1998

[54] SNAP-IN CONNECTION ASSEMBLY FOR EXTENSION GUIDEWIRE SYSTEM

[75] Inventors: Fausto Montano, Jr., Palm Springs North; Fernando M. Viera, Hialeah, both of Fla.

[73] Assignee: Cordis Corporation, Miami Lakes, Fla.

[21] Appl. No.: 807,997

[22] Filed: Mar. 3, 1997

Related U.S. Application Data

[63] Continuation of Ser. No. 579,920, Dec. 28, 1995, abandoned, which is a continuation of Ser. No. 88,618, Jul. 6, 1993, abandoned, which is a continuation of Ser. No. 734,718, Jul. 23, 1991, abandoned.

[51] Int. Cl.$^6$ ........................................................ A61B 5/00
[52] U.S. Cl. ............................................. 128/772; 128/657
[58] Field of Search .................................. 128/772, 657; 604/164, 95, 283; 285/260, 304, 321, 382.4, 921

[56] References Cited

U.S. PATENT DOCUMENTS

| | | | |
|---|---|---|---|
| 2,812,958 | 11/1957 | Rogers | 285/321 |
| 3,447,819 | 6/1969 | Borsum et al. | 285/321 |
| 3,784,235 | 1/1974 | Kessler et al. | 285/921 |
| 4,429,856 | 2/1984 | Jackson | 251/149.1 |
| 4,523,780 | 6/1985 | Cheer | 285/399 |
| 4,573,978 | 3/1986 | Reilly | 604/240 |
| 4,771,500 | 9/1988 | Kovacs . | |
| 4,827,941 | 5/1989 | Taylor et al. | 128/657 |
| 4,846,193 | 7/1989 | Tremulis et al. | 128/772 |
| 4,875,489 | 10/1989 | Messner et al. | 128/772 |
| 4,907,332 | 3/1990 | Christian et al. . | |
| 4,917,103 | 4/1990 | Gambale et al. | 128/772 |
| 4,922,923 | 5/1990 | Gambale et al. | 128/772 |
| 4,955,858 | 9/1990 | Drews | 604/8 |
| 4,966,163 | 10/1990 | Kraus et al. | 128/772 |
| 5,031,636 | 7/1991 | Gambale et al. | 128/772 |
| 5,035,686 | 7/1991 | Crittenden et al. | 604/96 |
| 5,037,391 | 8/1991 | Hammerslag et al. | 604/95 |
| 5,060,660 | 10/1991 | Gambale et al. | 128/772 |
| 5,109,867 | 5/1992 | Twyford, Jr. | 128/772 |
| 5,113,872 | 5/1992 | Jahrmarkt et al. | 128/772 |
| 5,117,838 | 6/1992 | Palmer et al. | 128/772 |
| 5,139,032 | 8/1992 | Jahmarkt et al. | 128/772 |
| 5,197,486 | 3/1993 | Frassica | 128/772 |

OTHER PUBLICATIONS

"Guide Wire Extension", Constantin Cope, M.D., *Radiology*, (1985); 157:263, p. 263.
"An Extra–Long Guide Wire For Use During Cardiac Catherization", Robert J. Adolph, M.D. & Ralph Shabetai, M.D., *Angiology*, (1966), 17:119–120, pp. 119–120.

*Primary Examiner*—Guy V. Tucker
*Attorney, Agent, or Firm*—Thomas R. Vigil

[57] ABSTRACT

The extension guidewire system is used with an inserted guidewire, such as used in a PTCA dilatation balloon catheter system, and includes a snap-connector assembly at and between a distal end of an extension guidewire and a proximal end of an initially inserted guidewire. The connector assembly comprises a snap-in sleeve mounted at the distal end of the extension guidewire, locking structure on the proximal end portion of the initially inserted guidewire and a radially inwardly extended detent on the snap-in sleeve positioned to engage in a gripping manner, and lock against, the locking structure on the proximal end of the initially inserted guidewire.

20 Claims, 4 Drawing Sheets

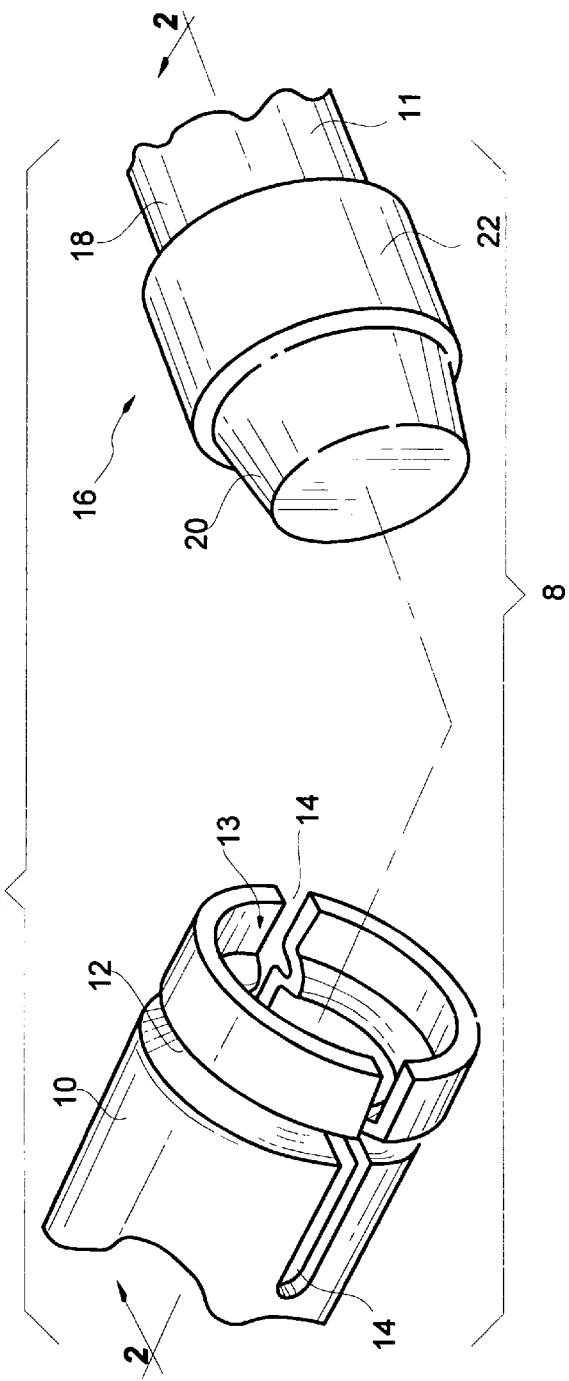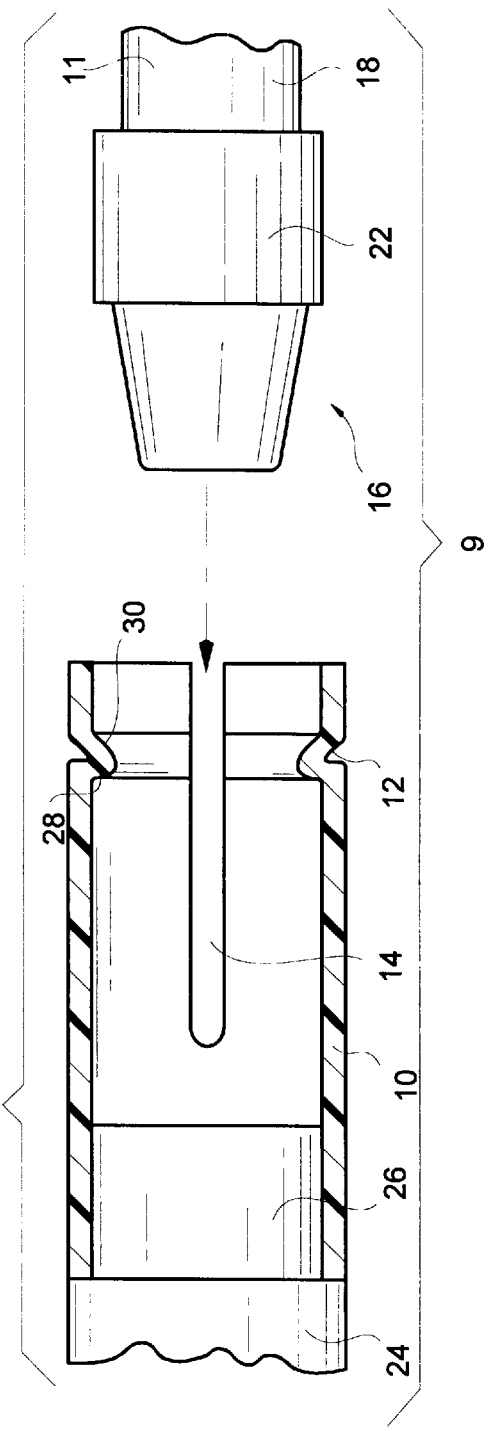

SNAP-IN CONNECTION ASSEMBLY FOR EXTENSION GUIDEWIRE SYSTEM

This is a continuation of application Ser. No. 08/579,920 filed Dec. 28, 1995, now abandoned, which is a continuation of Ser. No. 08/088,618 filed Jul. 6, 1993, now abandoned, which is a continuation of Ser. No. 07/734,71 filed Jul. 23, 1991, now abandoned.

BACKGROUND OF THE INVENTION

1. Field of the Invention.

The present invention relates to a snap-in connector assembly for an extension guidewire system for use with an inserted guidewire such as used in a PTCA dilatation balloon catheter system. More specifically, the present invention relates to a snap-in sleeve at the distal end of an extension guidewire for releasably and firmly connecting to a proximal end of an initially inserted guidewire, or vice versa, such a guidewire having a dilatation balloon catheter positioned thereon and situated within a guiding catheter inserted into a femoral artery or a carotid artery, for enabling the dilatation balloon catheter to be removed and replaced with another dilatation balloon catheter.

2. Description of the related art including information disclosed under 37 CFR §§ 1.97–1.99.

Heretofore, it has been proposed to provide an extension guidewire which is connected to an initially inserted guidewire to enable a balloon catheter of one size positioned in a vessel to be removed over the connected extension guidewire and replaced with another size balloon catheter.

Some examples of these previously proposed extension guidewire systems are disclosed in the following patents:

| U.S. Pat. No. | Patentee |
|---|---|
| 4,827,941 | Taylor et al |
| 4,846,193 | Tremulis et al |
| 4,875,489 | Messner et al |
| 4,922,923 | Gambale et al |

The Taylor et al U.S. Pat. No. 4,827,941 discloses an extendable guidewire system for introducing a dilatation catheter into the cardiovascular system. The guidewire has extension sections with a connection therebetween which permits the two sections to be joined together and separated simply by pushing the two sections together and pulling them apart. The connection between the guidewire sections comprise a tubular member which is fixed to the distal end of one guidewire extension section and which receives frictionally an interfitting undulating member extending from the proximal end of the other guidewire section.

An extendable telescoping guidewire and a method for introducing and exchanging catheters in vascular procedures is disclosed in the Tremulis et al U.S. Pat. No. 4,846,193. This guidewire has first and second interfitting sections moveable between extended and retracted positions relative to each other and means to releasably secure the two sections in the extended position.

Further, an extendable guidewire for introducing a dilatation catheter into a cardiovascular system has been proposed in the Messner et al U.S. Pat. No. 4,875,489 where the proximal end of a main guidewire has a tapered end portion which is received into a tubular member having a slit or slot therein which permits it to expand, the tubular member being received within an outer sleeve and fixed to a reduced in diameter distal end of a section of an auxiliary guidewire.

Also, an extendable guidewire system has been proposed in the Gambale et al U.S. Pat. No. 4,922,923. Here, the proximal end of the guidewire and the distal end of the exchange wire are formed to define a connection which may be crimped to effect the connection between the two wires. A crimping tool is provided to hold the mating ends of the guidewire and extension wire together while effecting the crimp.

The extension guidewire system of a catheter according to the present invention, is significantly different from the prior Taylor et al, Tremulis et al, Messner et al and Gambale et al guidewire extensions.

As will be described in greater detail hereinafter, the extension guidewire system of the present invention provides a simple connector assembly including a snap-in or snap-fit sleeve with locking means for quickly and firmly connecting an extension guidewire to the proximal end of an initially inserted guidewire and which permits quick and simple disengagement of the initially inserted guidewire from the connector assembly.

SUMMARY OF THE INVENTION

According to the present invention there is provided a p snap-in connector sleeve for an extension guidewire system of the present invention which provides a new and improved extension guidewire for a PTCA dilatation balloon catheter for enabling a dilatation balloon catheter to be removed and replaced with another dilatation balloon catheter. More specifically, the snap-in sleeve is mounted to a distal end of an extension guidewire which is adapted to be releasably but firmly connected to a proximal end of an initially inserted guidewire. The snap-in sleeve has one or two longitudinal slots therein to permit expansion of the sleeve and has at least one inwardly extending detent for locking behind a shoulder provided on the proximal end of the initially inserted guidewire when the initially inserted guidewire is inserted into the sleeve. The initially inserted guidewire has a shoulder on its proximal end and the snap-in sleeve is constructed and arranged to receive and lock against the shoulder.

BRIEF DESCRIPTION OF THE DRAWINGS

FIG. 1 is a perspective view of the snap-in connector assembly for an extension guidewire system constructed according to the teachings of the present invention.

FIG. 2 is a sectional view of two parts of the connector assembly shown in FIG. 1, taken along line 2—2 of FIG. 1 and shows the two parts positioned for connection to each other.

DESCRIPTION OF THE PREFERRED EMBODIMENT(S)

Figure 3:
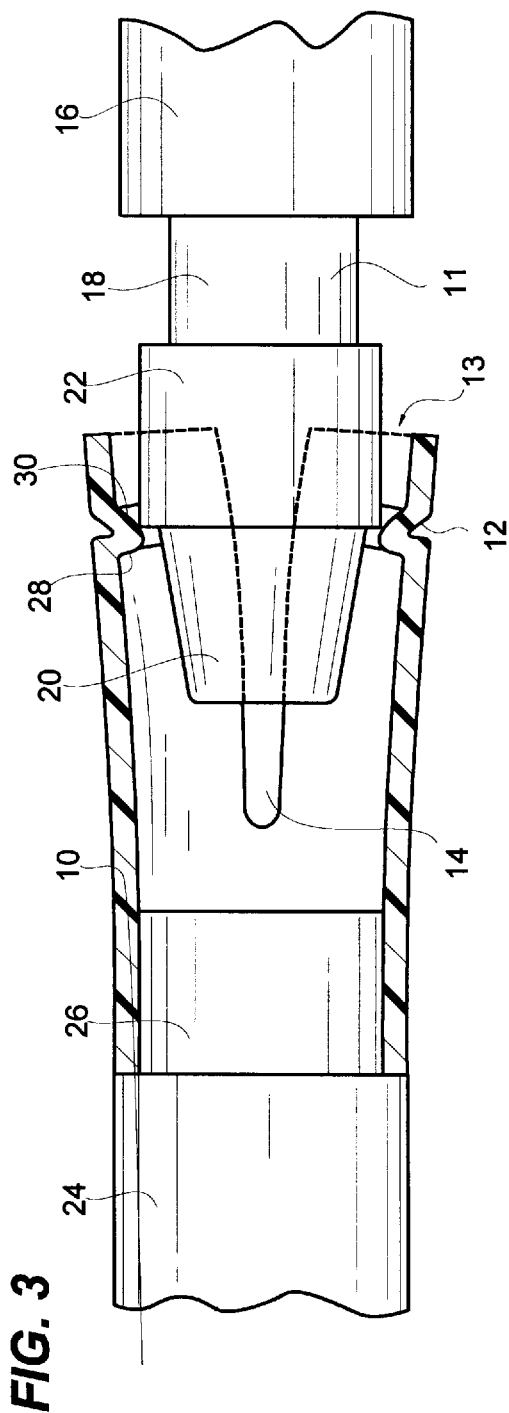
FIG. 3 is a sectional view of the two parts of the snap-in connector assembly shown in FIG. 2 as they are being connected together.

The extension guidewire system of the present invention can be used, for example, in a PTCA dilatation balloon catheter. In use, the distal end portion of the balloon catheter including a guidewire is moved into an area of stenosis within a blood vessel. Then, a dilatation fluid is supplied through the catheter to the balloon to expand the balloon against the walls of the blood vessel thereby to open the restricted passageway through the stenotic area. Once this has been achieved, the balloon catheter can be withdrawn.

Often the balloon catheter chosen is the wrong size, the balloon being too small or too large. When this occurs, it is necessary to remove the balloon catheter and replace the same with a new balloon catheter. However, the length of the guidewire is such that the balloon catheter including the guidewire have to be removed and replaced with a new balloon catheter and guidewire. This is a tedious, painstaking and time consuming task, as well as unsafe, and it is easier if the initial guidewire can be left in place with the initially inserted balloon catheter being removed and then replaced with a new balloon catheter. To enable the old guidewire to be utilized, techniques have been developed for using an exchange guidewire or an extension guidewire which is capable of being attached and detached from the proximal end of the initially inserted guidewire.

It is desirable that the connection or attachment of such an extension guidewire be simple and be easily detachable while maintaining a firm attachment or connection between the extension guidewire and the initially inserted guidewire.

A snap-in connector assembly 8 of an extension guidewire system 9 for connecting to the proximal end of an inserted guidewire to an extension guidewire, constructed according to the teachings of the present invention, for achieving this function, is shown in FIGS. 1–4.

Referring now to the drawings in greater detail there is illustrated in FIGS. 1–4 a first embodiment of the extension guidewire system 9. FIG. 1 shows the extension guidewire system 9 in perspective view with two parts 10 and 11 of the snap-in connector assembly 8 separated from each other. The part 10 is a snap-in sleeve 10 having an outer diameter of from approximately 0.010 inch to 0.018 inch. An annular depression is formed in the sleeve 10 to create an inwardly extending detent 12, at a distance of approximately 0.003 to 0.500 inch from a distal open end 13 of the sleeve 10. The sleeve 10 also has at least one and preferable two diametrically opposed, longitudinally extending slot(s) 14 that extend rearwardly, a length of from approximately 0.02 inch to 0.50 inch, from the sleeve distal end 13. The slot or slots 14 facilitate elastic deformation of the sleeve 10 when inserting or removing the proximal end portion of the other guidewire.

An initially inserted guidewire 16 has a proximal end portion 18 that defines the second part 11 of the connector assembly 8. The reduced in diameter proximal end portion 18 has an outer diameter slightly smaller than the inner diameter of the annular detent 12. The proximal end portion 18 also has a tapered end 20 and a band 22 which is fixed on the reduced-in-diameter end portion 18 adjacent to the tapered end 20 and has an outer diameter slightly smaller than the inner diameter of the snap-in sleeve 10.

The snap-in sleeve 10 is fixed to an extension guidewire 24, namely to a reduced-in-diameter distal end portion 26 of the guidewire 24, and is welded thereto as shown in FIG. 2.

The annular detent 12 is formed asymmetrically with the radially inwardly extending surface 28 facing toward the distal end portion 26 of the guidewire 24 and with an inclined surface 30 extending axially and radially outwardly from the surface 28 to the inner diameter surface of the sleeve 10 and toward the part 11 as shown in the sectional view of the extension guidewire system 9 in FIG. 2.

Figure 4:
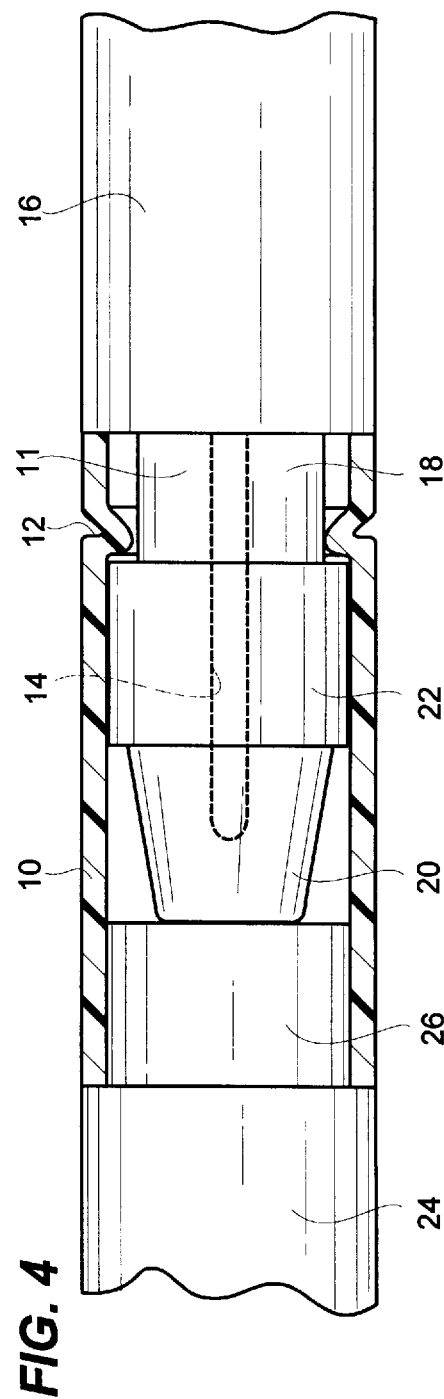
FIG. 4 is a sectional view of the snap-in connector assembly shown in FIG. 2 but in a connected position.

In FIGS. 2–4, the connection procedure for connecting the parts 10 and 11 of the connector assembly 8 is illustrated. As shown, the part 11 (proximal end portion 18) is inserted into the part 10 (snap-in sleeve 10) by pushing the proximal end portion 18 of the guidewire 16 into the snap-in sleeve 10 fixed to the extension guidewire 24. The tapered end 20 and the band 22 on the proximal end portion 18 of the guidewire 16 forces the sleeve 10 open as shown in FIG. 3. Once the band 20 has passed the annular detent 12, the snap-in sleeve 10 snaps back to its initial position and the guidewires 16 and 24 are locked together.

The inclined surface 30 of the annular detent 12 facilitates easy insertion of the proximal end portion 18 into the sleeve 10 and the flat radially inwardly extending surface 28 abuts flat against an edge of the band 20 to ensure a secure locking of the sleeve 10 to the proximal end portion 18 by the engagement of the wall surface 28 of the detent 12 against the band 20 and by engagement of an outer free end of the sleeve 10 against a side wall of the reduced-in-diameter portion 18 adjacent the guidewire 16 as shown in FIG. 4.

Figure 5:
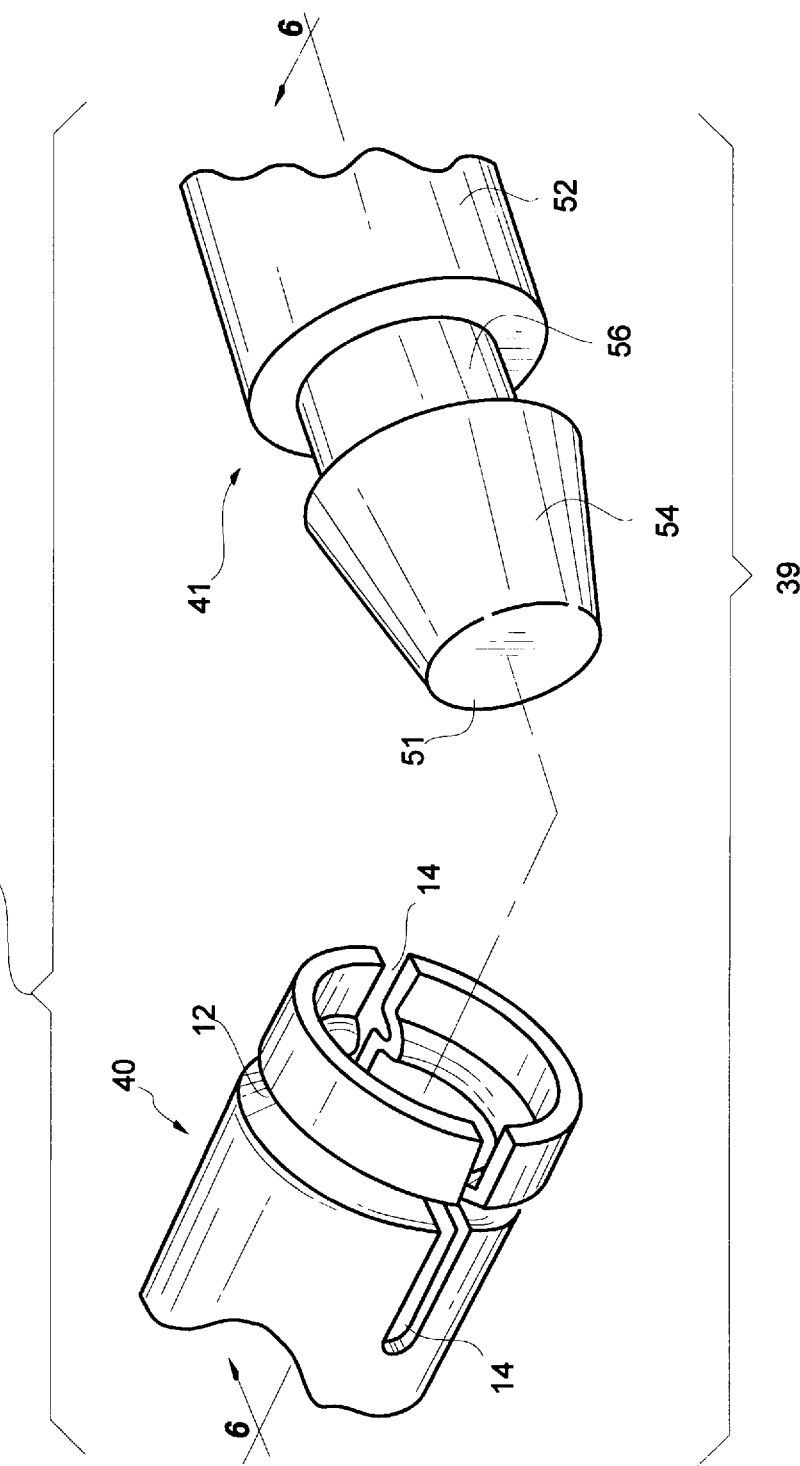
FIG. 5 is a perspective view of another embodiment of the snap-in connector assembly constructed according to the teachings of the present invention prior to connection of the two parts thereof.
Figure 6:
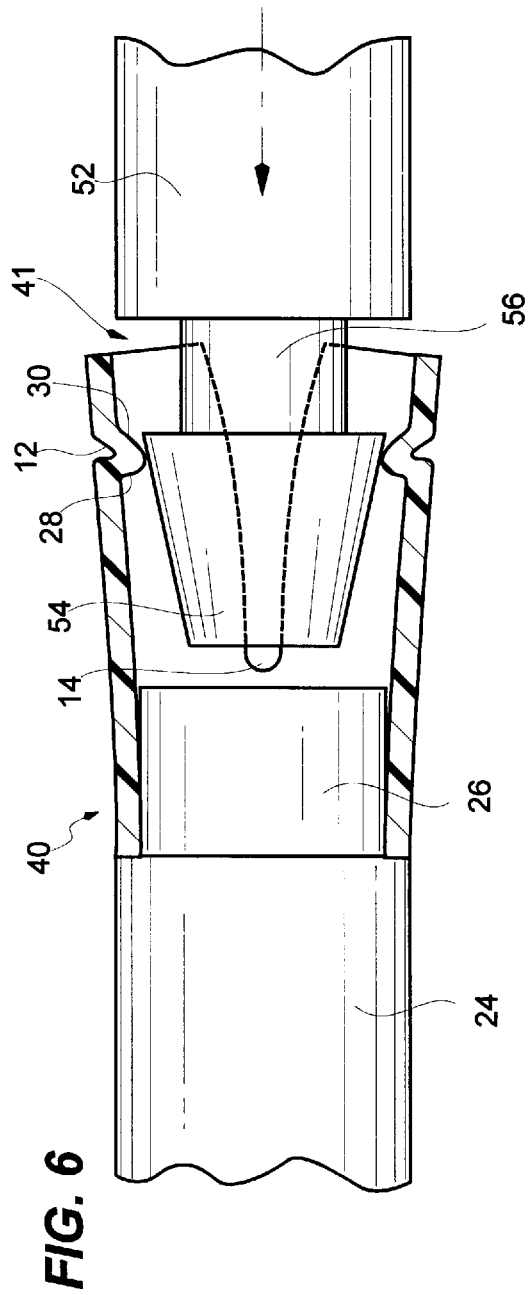
FIG. 6 is a sectional view of the two parts of the snap-in connector assembly shown in FIG. 5, taken along line 5—5 of FIG. 5 and shows the parts prior to connection thereof.
Figure 7:
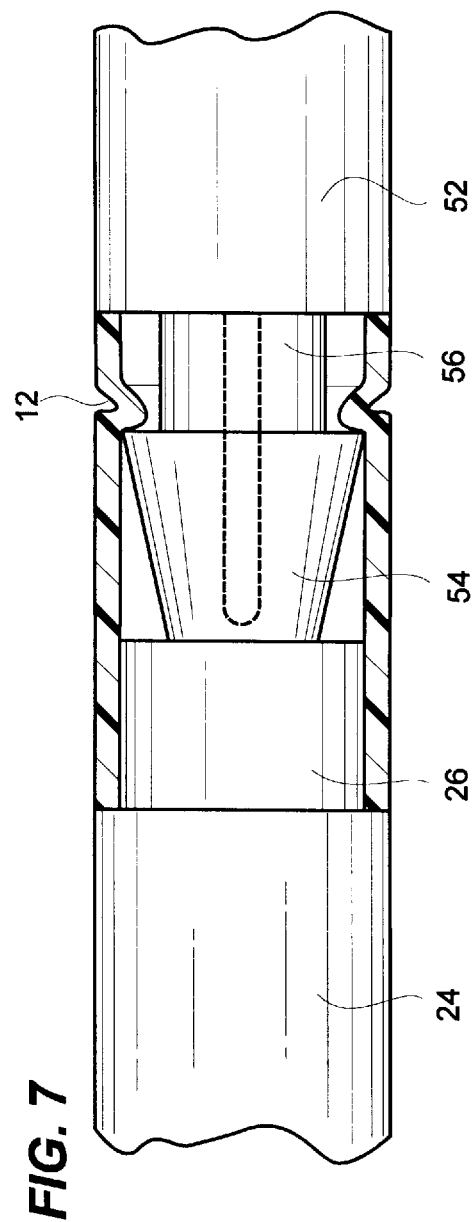
FIG. 7 is a sectional view of the snap-in connector assembly shown in FIG. 5 but shows the parts thereof in a connection position.

FIGS. 5–7 show another embodiment of a snap-in connector assembly 38 of an extension guidewire system 39 constructed according to the teachings of the present invention. FIG. 5 is a perspective view of the extension guidewire system 39 and shows two parts 40 and 41 thereof disconnected.

The sleeve 40 is identical to the part 10 namely the snap-in sleeve 10.

The port 41 which is to be inserted into the snap-in sleeve 40 is defined by a specially cut proximal end 51 of an initially inserted guidewire 52 has a cone 54 at the end thereof and an annular groove 56 cut therein between the cone 54 and the remainder of the guidewire 52 whereby the greatest outer diameter of the cone 54 adjacent the groove 56 is slightly smaller than the inner diameter of the sleeve 40 and the outer diameter of the groove 56 is slightly smaller than the inner diameter of the annular detent 12.

It will be understood that the part 41 is inserted into the part 40 (sleeve 40) in the same way as the part 11 is inserted into the part 10 as described above with reference to FIGS. 1–4. The guidewires are locked together by the engagement of the annular wall surface 28 of the detent 12 against the side wall of the annular groove 56 adjacent the cone 54 and by engagement of the outer free end of the sleeve 40 against the opposite side wall of the annular groove 56 adjacent the guidewire 52 as shown in FIG. 7.

The extension guidewire system 9 or 39 including the snap-in connector assembly 8 or 38 is made out of medically suitable material for inserting into the human body, such as stainless steel or equivalent.

It will be understood that the snap-in sleeve 10 or 40 can be secured to the proximal end of the initially inserted guidewire instead of to the distal end of the extension guidewire and that the distal end of the extension guidewire can be formed in the manner of the part 11 or the part 41. In other words, the parts 10, 40 and 11, 41 can be reversed respectively on the initially inserted guidewire and the extension guidewire.

From the foregoing description it will be understood that the snap-in connector assembly 10 or 40 of the present invention has a number of advantages some of which have been described above and others of which are inherent in the invention. Accordingly, the scope of the invention is only to be limited as necessitated by the accompanying claims.

We claim:

1. An extension guidewire system comprising an initially inserted guidewire having a proximal end and a proximal end portion, an extension guidewire adapted to be connected axially to said proximal end portion of said initially inserted guidewire, and a connector assembly not including a retractable spring biased sleeve;

said extension guidewire having a distal end, a distal end portion and a proximal end; and said connector assembly consisting essentially of:

a snap-in sleeve or tube which is made from a medically suitable metal tubing and which is mounted at one of the distal end of said extension guidewire and the proximal end of said initially inserted guidewire;

an engageable means on one of said proximal end portion of said initially inserted guidewire and said distal end portion of said extension guidewire for axially engaging and elastically deforming said snap-in sleeve when at least one of said engageable means and said snap-in sleeve is moved relative to the other in an axial direction only; and a radially inwardly extending detent in said snap-in tube which is positioned to engage against and lock with said engageable means on the other of said proximal end portion of the initially inserted guidewire and said distal end portion of said extension guidewire upon relative axial movement of said proximal end portion of the initially inserted guidewire and of said distal end of said extension guidewire and said snap-in tube toward, and into engagement with, each other followed by substantial elastic recovery of said snap-in sleeve when said detent moves into engagement with said engagable means, and said snap-in sleeve and said engageable means being disengagable upon axially pulling them apart.

2. The extension guidewire system of claim 1 wherein said snap-in tube has at least one longitudinal slot extending axially from a free end of said tube part way into said tube to permit expansion of said tube and having an outer diameter generally equal to the outer diameter of said guidewires.

3. The extension guidewire system of claim 2 wherein the length of said slot is between 0.02 inch and 0.50 inch.

4. The extension guidewire system of claim 2 wherein the distance of said detent from the outer end of said tube is between 0.003 inch and 0.500 inch.

5. The extension guidewire system of claim 1 wherein said snap-in tube is mounted on a reduced-in-diameter distal end of said extension guidewire or proximal end of said initially inserted guidewire.

6. The extension guidewire system of claim 1 wherein one of said proximal end portion or said distal end portion has a reduced-in-diameter section and said engageable means comprises an annular band mounted on said reduced-in-diameter section of said proximal end portion of said initially inserted guidewire or of said distal end portion of said extension guidewire.

7. The extension guidewire system of claim 6 wherein said detent is annular and said reduced-in-diameter section of said proximal end portion of said initially inserted guidewire or of said extension guidewire has an outer diameter slightly smaller than the inner diameter of said annular detent.

8. The extension guidewire system of claim 6 wherein said reduced-in-diameter proximal end portion or distal end portion has a tapered end.

9. The extension guidewire system of claim 8 wherein said annular band has an outer diameter slightly smaller than the inner diameter of said snap-in tube and is located next to said tapered end on said proximal end portion or said distal end portion.

10. The extension guidewire system of claim 1 wherein said engageable means comprises a cone at the outer end of said proximal end portion of said initially inserted guidewire or at the outer end of said of said distal end portion of said extension guidewire and an annular groove which is cut into said proximal end portion adjacent a base of said cone and defining a reduced in cross section area.

11. The extension guidewire system of claim 10 wherein the largest outer diameter at the base of said cone is slightly smaller than the inner diameter of said snap-in sleeve or tube and the outer diameter of said groove is slightly smaller than the inner diameter of said detent.

12. The extension guidewire system of claim 1 wherein said detent is a radially inwardly extending annular detent having a flat radially inwardly extending surface facing toward said distal end of said extension guidewire or toward said proximal end of said initially inserted guidewire and an inclined surface extending axially and radially outwardly to the inner surface of said snap-in tube and facing toward the open outer end of said tube for facilitating easy insertion of said proximal end portion or said distal end portion into said sleeve and said flat, radially inwardly extending surface abuts against said engageable means to ensure a good engagement and locking of said snap-in tube to one of said proximal end portion and to said distal end portion.

13. The extension guidewire system of claim 1 wherein said snap-in sleeve and said engageable means are made out of medically suitable material for insertion into the human body.

14. The extension guidewire system of claim 13 wherein said medically suitable material is stainless steel.

15. A method for connecting and disconnecting an extension guidewire to an initially inserted guidewire without use of a retractable spring biased sleeve, said method consisting essentially of the steps of:

providing a length of extension guidewire;

providing a snap-in sleeve or tube which is made from a medically suitable metal tubing and which is mounted on one of: the distal end of the extension guidewire and the proximal end of the initially inserted guidewire;

arranging the snap-in tube to receive, elastically deform and then grippingly engage an end of a guidewire followed by substantial elastic recovery of said snap-in tube;

axially inserting into the snap-in tube and causing elastic deformation of said tube the other of:

the proximal end of the initially inserted guidewire and the distal end of the extension guidewire, thereby to connect firmly the distal end of the extension guidewire to the proximal end of the initially inserted guidewire followed by substantial elastic recovery of said snap-in tube; and, when it is desired to disconnect the quidewires, axially pulling the quidewires apart.

16. An extension guidewire system comprising an initially inserted guidewire having a proximal end and a proximal end portion, an extension guidewire adapted to be connected to said proximal end portion of said initially inserted guidewire, and a connector assembly not including a retractable spring biased sleeve;

said extension guidewire having a distal end, a distal end portion and a proximal end; and said connector assembly comprising two pieces, namely:

a snap-in sleeve or tube which is made from a medically suitable metal tubing and which is mounted at one of the distal end of said extension guidewire and the proximal end of said initially inserted guidewire;

first engaging means on one of said proximal end portion of said initially inserted guidewire and said distal end portion of said extension guidewire;

second engaging means including a radially inwardly extending detent in said snap-in sleeve which is positioned to engage against and lock with said first engaging means on the other of the proximal end portion of the initially inserted guidewire and the distal end portion of said extension guidewire upon relative axial movement of said proximal end portion of the initially inserted guidewire and of the distal end of said extension guidewire and said snap-in sleeve toward, and into axial engagement with, each other, thereby causing elastic deformation of said snap-in sleeve, said sleeve including an annular wall which surrounds said first engaging means for preventing substantial radial movement between said first engaging means and said second engaging means, said detent of said second engaging means including at least one indentation in said annular wall extending radially inwardly from said annular wall to engage said first engaging means thereby allowing substantial elastic recovery of said snap-in sleeve, and said first engaging means only being removable from said sleeve in an axial direction with elastic deformation of said snap-in sleeve and not being removable in a radial direction.

17. The extension guidewire system of claim 16 wherein said indentation is a generally annularly extending indentation in said annular wall and forms an annular depression in said sleeve.

18. The extension guidewire system of claim 16 wherein said first engaging means include an annular recess or groove and side walls thereof in the end of the other of the two guidewires not having said sleeve thereon and the two guidewires are locked together against relative axial movement by the engagement of said detent against one side wall of said groove and by the engagement of a distal end of said sleeve against the other side wall of said groove adjacent the other of the guidewires.

19. The extension guidewire system of claim 16 wherein said sleeve is elastically deformable to allow said second engaging means to be moved into and to be moved out of said sleeve.

20. The extension guidewire system of claim 19 wherein said sleeve has at least one slot extending axially from a free end of said sleeve part way into said sleeve to facilitate elastic deformation of said sleeve.

* * * * *

UNITED STATES PATENT AND TRADEMARK OFFICE
CERTIFICATE OF CORRECTION

Page 1 of 2

PATENT NO. : 5,813,405
DATED : September 29, 1998
INVENTOR(S) : Fausto Montano, Jr. and Fernando M. Viera It is certified that error appears in the above-indentified patent and that said Letters Patent is hereby corrected as shown below:

On the title page:
Item[ 63 ]   please delete all references to related U.S. application data and insert the following in place thereof:

--Continuation of Ser. No. 579,920, Dec. 28, 1995, abandoned, which is a continuation of Ser. No. 88,618, Jul. 6, 1993, abandoned, which is a continuation of Ser. No. 734,718, Jul. 23, 1991, abandoned, which is a continuation-in-part of Ser. No. 510,522, Apr. 18, 1990, now U.S. Patent No. 5,139,032, and a continuation-in-part of Ser. No. 510,523, Apr. 18, 1990, now U.S. Patent No. 5,113,872.--

Column 1, lines 4-8, delete and substitute in place thereof:

--This application is a continuation of Ser. No. 08/579,920 filed Dec. 28, 1995, now abandoned, which is a continuation of Ser. No. 08/088,618 filed Jul. 6, 1993, now abandoned, which is a continuation of Ser. No. 07/734,718 filed Jul. 23, 1991, now abandoned, which is a continuation-in-part of Ser. No. 07/510,522 filed April 18, 1990, now U.S. Patent No. 5,149,032, issued August 18, 1992, and a continuation-in-part of Ser. No. 07/510,523 filed Apr. 18, 1990, now U.S. Patent No. 5,113,872 issued May 19, 1992.--

UNITED STATES PATENT AND TRADEMARK OFFICE
CERTIFICATE OF CORRECTION

PATENT NO. : 5,813,405
DATED : September 29, 1998
INVENTOR(S) : Fausto Montano, Jr. and Fernando M. Viera It is certified that error appears in the above-indentified patent and that said Letters Patent is hereby corrected as shown below:

Column 2, line 22, delete "p".

Column 2, line 52, ";" should be --.--.

Column 3, line 24, after "detachable" insert --by pulling the guidewires axially away from each other--.

Column 3, line 42, "preferable" should be --preferably--.

Column 4, line 29, "port" should be --part--.

Column 6, line 4, delete "of said", second occurrence.

Column 6, line 53, "quidewires", both occurrences, should be --guidewires--.

Signed and Sealed this

Fifteenth Day of June, 1999

Attest:

Q. TODD DICKINSON

*Attesting Officer*    *Acting Commissioner of Patents and Trademarks*